(12) United States Patent
Khachik

(10) Patent No.: US 7,119,238 B2
(45) Date of Patent: Oct. 10, 2006

(54) PROCESS FOR PURIFICATION AND CRYSTALLIZATION OF PALM OIL CAROTENOIDS

(75) Inventor: Frederick Khachik, Rockville, MD (US)

(73) Assignee: University of Maryland, College Park, MD (US)

( * ) Notice: Subject to any disclaimer, the term of this patent is extended or adjusted under 35 U.S.C. 154(b) by 217 days.

(21) Appl. No.: 10/332,700

(22) PCT Filed: Jul. 11, 2001

(86) PCT No.: PCT/US01/41332

§ 371 (c)(1),
(2), (4) Date: Jan. 13, 2003

(87) PCT Pub. No.: WO02/04415

PCT Pub. Date: Jan. 17, 2002

(65) Prior Publication Data

US 2003/0158455 A1 Aug. 21, 2003

Related U.S. Application Data

(60) Provisional application No. 60/217,585, filed on Jul. 12, 2000.

(51) Int. Cl.
*C07C 13/20* (2006.01)
(52) U.S. Cl. ........................................................ 585/23
(58) Field of Classification Search ................... 585/23
See application file for complete search history.

(56) References Cited

U.S. PATENT DOCUMENTS

| 243,021 A | * | 6/1881 | Larner | ........................ 428/28 |
| 5,019,668 A | | 5/1991 | Keat et al. | |
| 5,157,132 A | | 10/1992 | Tan et al. | |
| 5,382,714 A | | 1/1995 | Khachik | |
| 5,902,890 A | | 5/1999 | Nitsche et al. | |
| 2005/0038271 A1 | | 2/2005 | Khachik | |

FOREIGN PATENT DOCUMENTS

| EP | 0 242 148 B1 | 10/1987 |
| EP | 0 349 138 B1 | 8/1994 |
| GB | 1 515 238 | 6/1978 |
| GB | 2 160 874 A | 1/1986 |
| GB | 2 218 898 A | 11/1989 |
| JP | 61-109764 | 5/1986 |
| JP | 07-304978 | 11/1995 |
| WO | WO 98/03480 A1 | 1/1998 |
| WO | WO 99/20587 A1 | 4/1999 |

OTHER PUBLICATIONS

Auweter, H., et al., "Supramolecular Structure of Precipitated Nanosize β-Carotene Particles," *Angew. Chem. Int. Ed.* 38:2188-2191, Wiley-Vch Verlag GmbH (Aug. 1999).

Gordon, A.J. and Ford, R.A., eds. "Low-Temperature Baths," in: *The Chemist's Companion*, John Wiley & Sons, New York, NY, pp. 451-452 (1972).

Khachik, F., et al., "Identification, Quantification, and Relative Concentrations of Carotenoids and Their Metabolites in Human Milk and Serum," *Anal. Chem.* 69:1873-1881, American Chemical Society (1997).

Lenfant, C. and Thyrion, F.C., "Extraction of carotenoids from palm oil. II. Isolation methods," *Oléagineux Corps gras Lipides* 3:294-307, John Libbey Eurotext (1996).

Murakoshi, M., et al., "Potent Preventive Action of α-Carotene against Carcinogenesis: Spontaneous Liver Carcinogenesis and Promoting Stage of Lung and Skin Carcinogenesis in Mice Are Suppressed More Effectively by α-Carotene Than by β-Carotene," *Cancer Res.* 52:6583-6587, American Association for Cancer Research (1992).

Patent Abstracts of Japan, English language abstract of JP 61-109764 (Document AN1) (1998).

Patent Abstracts of Japan, English language abstract of JP 07-304978 (Document AL2) (1998).

International Search Report for International Application No. PCT/US01/41332, mailed Jul. 3, 2002.

* cited by examiner

*Primary Examiner*—Shailendra Kumar
(74) *Attorney, Agent, or Firm*—Sterne, Kessler, Goldstein & Fox P.L.L.C.

(57) ABSTRACT

Disclosed is a process for purification of a mixture of carotenoids from palm oil concentrate to produce a crystalline mixture of a α-carotene, β-carotene, γ-carotene, and ε,ε-carotene as well as a product enriched in geometrical isomers of a β-carotene (9-cis-β-carotene, 13-cis-β-carotene) and α-carotene as well as ε,ε-carotene and γ-carotene.

13 Claims, No Drawings

PROCESS FOR PURIFICATION AND CRYSTALLIZATION OF PALM OIL CAROTENOIDS

This application is a 371 of PCT/US01/41332, filed Jul. 11, 2001, which claims benefit of 60/217,585, filed Jul. 12, 2000.

BACKGROUND OF THE INVENTION

1. Field of the Invention

The invention is in the field of natural products chemistry. In particular, disclosed is a process for purification of a mixture of carotenoids from palm oil concentrate to produce a crystalline mixture of α-carotene, β-carotene, γ-carotene, and ε,ε-carotene as well as a product enriched in geometrical isomers of β-carotene (9-cis-β-carotene, 13-cis-β-carotene) and α-carotene as well as ε,ε-carotene and γ-carotene.

2. Related Art

The total concentration of carotenoids in crude palm oil is quite low, i.e., approximately 710 ppm. The major carotenoids in palm oil are α-carotene and β-carotene and to a lesser extent γ-carotene. Minor quantities of ε,ε-carotene, a cis-isomer of α-carotene, 9-cis-β-carotene, and 13-cis-β-carotene are also present in palm oil. Since with the exception of ε,ε-carotene, the rest of these carotenoids are precursors of vitamin A, crude palm oil is commercially processed to remove most of the oils and produce a product which is highly concentrated in carotenes. The resulting palm oil carotene concentrate is currently used as a nutritional supplement as well as a food coloring additive. In the course of the past several decades numerous extraction methods have been developed to recover the carotenoids from crude palm oil (GB 1515238 (1976), JP 61109764 (1986), GB 2160874 (1986), EP 0242148 (1987), AU App. No P18770/88 (1988), GB 2218989 (1989), U.S. Pat. No. 5,157,132 (1992)). The classification and assessment of the proposed and patented methods for the industrial production of palm carotenes has been published in a review article by Lenfant and Thyrion OCL-Oleagineux Corps Gras lipides, 3: (4) 294–307, 1996. Because the exposure of carotenoids to oxidizing species present in air, as well as heat, light, and acids results in degradation and losses of these compounds, many of the proposed refining processes for industrial production of a carotene-rich palm oil concentrate are not economically viable. The Lion Corporation of Japan has successfully developed a unique patented process that produces several carotene-rich palm oil concentrate ranging from 2% to 30%. In the initial step of this process, most of the fats and oils are removed by solvolytic micellization (JP 61109764 (1986), BP 2160874 (1986), EP 0242148 (1987)). This results in a palm oil concentrate with 2% carotene content which is then subjected to molecular distillation to remove the volatile oils. As a result, a palm oil carotene concentrate is obtained with a total carotene content of approximately 20%. In the final step of this process developed by Lion, the palm oil carotene concentrate is purified to greater than 95% by chromatography on industrial scale to give a crystalline mixture of carotenoids (EP 0242148 (1987)). The resulting mixture of carotenoids is suspended in vegetable oil to produce the commercial palm oil carotene concentrate with a total carotene content of 30%. To date, the process developed by Lion remains as the only commercial source for the production of a crystalline mixture of palm oil carotenoids with a purity in excess of 95%. The only drawback with this method is that the chromatographic purification of carotenoids by this technique on an industrial scale is quite costly. Another commercially available palm oil concentrate with approximately 20% total carotene content is produced in Malaysia according to a proprietary process; this process does not isolate a crystalline mixture of carotenoids.

As mentioned above, palm oil carotenoids include (6'R)-β,ε-carotene (α-carotene), β-carotene (trans+cis), ε,ε-carotene, and γ-carotene. While numerous synthetic methods have been developed for the laboratory and pilot plant scale preparation of these carotenoids, only β-carotene is currently manufactured on industrial scale. Synthetic methods for commercial production of carotenoids are quite costly because they involve numerous steps in which the precursors to these compounds have to be purified to remove the unchanged starting materials and the undesirable side products. In addition, these synthetic pathways normally use organic reagents, which are toxic and harmful to humans. Therefore, the presence of possible residual contaminants in carotenoids prepared by synthesis is a major deficiency and concern with products of this nature.

Among the carotenoids isolated from palm oil, α-carotene has been shown to serve as an excellent cancer chemopreventive agent in comparison with β-carotene (Murakoshi et al. Cancer Research, 52: 6583–87, 1992). In the above study, the potent preventive action of α-carotene against spontaneous liver carcinogenesis and promoting stage of lung and skin carcinogenesis in mice were suppressed more effectively by α-carotene than by β-carotene. Other than the chromatographic procedure employed by Lion, crystalline palm oil carotenoids which, in addition to β-carotene, include α-carotene and γ-carotene are not commercially available by any other means. In addition, the natural form of α-carotene [(6'R)-β,ε-carotene] is optically active and as a result its commercial preparation by known synthetic procedures is not economical.

This invention was developed because there are no reports on purification of carotenoids from palm oil concentrates that separates the crystalline carotenes from oil by a simple method. The purification and isolation of palm oil carotenoids in crystalline form allows the micronization of these pigments into water dispersible beadlet which is the most preferred formulation for carotenoids as a nutritional supplement (Auweter et al., Angew. Chem. Ind. Ed. 38: 2188–2191, 1999). The process described here provides a convenient and an economical route to purification of a crystalline mixture of carotenoids from commercial palm oil with 2% and 20% total carotene content. This process has also been successfully employed to remove the vegetable oil from the 30% commercial palm oil carotene and recovers a crystalline mixture of carotenoids in excellent purity.

SUMMARY OF THE INVENTION

To obtain the crystalline carotenoids from palm oil with about 2% carotene content, a solution of the oil in an organic solvent may first be subjected to alkaline hydrolysis (saponification) to remove the oils and after work-up, the total carotene content in the crude product is increased to about 49–55%. This product consists of a mixture of α-carotene, a cis-isomer of α-carotene, all-trans-β-carotene, 9-cis-β-carotene, 13-cis-β-carotene, γ-carotene, and ε,ε-carotene. The solids are then subjected to crystallization with acetone and an alcohol at low temperature (e.g., about –15° C. or lower) or tetrahydrofuran (THF) and an alcohol at about –40° C. or lower. Alternatively, a combination of a chlorinated solvent and an alcohol at low temperature (e.g., about –40° C. or lower) can also be employed as crystallization solvents. After this crystallization, the purity of carotenes in the mixture is increased to about 76–80%. At this stage, the overall recovery of carotenes based on the starting material (palm carotene with about 2% carotene content) was in the range of about 77–80%. A second crystallization afforded the carotenes in purity of about 93% or greater. The mother liquor from first crystallization contained substantial quantities of 9-cis-β-carotene and 13-cis-β-carotene as well as a cis-isomer of α-carotene.

In the case of the palm oil with about 20% to about 30% carotene content, the above saponification step can be omitted and the oils can be directly subjected to crystallization. In a typical experiment, palm oil is dissolved in tetrahydrofuran (THF)/acetone or in a chlorinated solvent. The mixture is stirred for about 15 minutes at room temperature and is treated with an alcohol until the solution becomes cloudy. After cooling to about −40° C. or lower for 5 hours, the yellow/orange crystals of palm carotenes are then quickly filtered at about −20° C. or lower. The collected crystals are washed with cold alcohol and dried under high vacuum.

Thus, the invention is directed to a process for isolation of a mixture of carotenes from palm oil, comprising saponifying an organic solution of the said palm oil with an alcoholic (methanol, ethanol, 2-propanol, etc.) solution of a mineral base such as potassium or sodium hydroxide and the like. Washing the organic layer with water containing 10–20% alcohol until the base is removed, separating and concentrating the resultant organic phase comprising isolated carotenes and optionally treating the organic phase with an alcohol with cooling to give crystalline carotenes.

The invention is also directed to a process for isolation of a mixture of carotenes from palm oil comprising about 20–30 wt % carotenes, comprising dissolving the palm oil in THF, acetone, a chlorinated solvent or mixtures thereof, followed by adding an alcohol, and keeping the solution at low temperature for a time sufficient to give a crystalline mixture of α-carotene, all-trans-β-carotene, 9-cis-β-carotene, 13-cis-β-carotene, ε,ε-carotene, and γ-carotene.

DETAILED DESCRIPTION OF THE INVENTION

A procedure for isolation and crystallization of carotenoids in high purity from commercially processed palm oil with about 2% to almost 30% carotene content has been developed. Palm oil carotenoids comprising of approximately ((6'R)-β,ε-carotene (α-carotene), 30.0%), all-trans-β-carotene (41.0%), 9-cis-β-carotene (11%), 13-cis-β-carotene (8%), ε,ε-carotene (2.0%), and γ-carotene (8.0%) can be obtained as a crystalline mixture free from oil in excellent purity. An organic solution of palm oil with about 2% carotene content in solvents such as tetrahydrofuran, tert-butylmethyl ether (TBME) or similar ethers is first saponified e.g. with about 10% ethanolic or methanolic potassium or sodium hydroxide and after work-up, carotenoids are obtained in about 49–55% purity. Crystallization of this crude product with acetone and an alcohol or tetrahydrofuran (THF) and an alcohol at about −40° C. or lower increases the purity of carotenes to about 76–80%. The purity of the carotenes can be increased to about 93% or greater with a second crystallization with the fore-mentioned solvents. In the case of palm oil with about 20% to about 30% carotene content, the saponification step may be eliminated and combinations of organic solvents such as THF, acetone, and an alcohol may be used as crystallization solvents. In a typical process, palm oil carotene concentrate is dissolved in tetrahydrofuran (THF) and acetone and the mixture of carotenoids are then crystallized by addition of an alcohol followed by cooling at low temperatures (about −40° C. or lower). In all cases, a chlorinated solvent and an alcohol at low temperatures can also be employed to yield crystalline carotenes from palm oil in high purity. Depending on the commercial source of the palm oil concentrate, the purity of the crystalline carotenes after the first crystallization is in the range of about 55–92%. During this process, substantial amount of geometrical isomers of β-carotene (9-cis-β-carotene, 13-cis-β-carotene) and a cis-isomer of α-carotene as well as ε,ε-carotene and γ-carotene which are present in the commercial palm oil concentrates are removed from the purified product and are concentrated in the mother liquor from crystallization. The purified mixture of carotenoids obtained by this method is free from oils and can be readily formulated into nutritional supplements for human use as well as providing a suitable and effective color additive for foods.

Alcohols which can be used in the process are preferably $C_{1-4}$ alcohols including methanol, ethanol, 2-propanol, and the like.

Chlorinated solvents which can be used in the process are preferably $C_{1-2}$ chlorinated solvents such as dichloromethane, chloroform, carbon tetrachloride, 1,2-dichloroethane and the like.

Ethers which can be used in the process are preferably $C_{4-10}$ ethers such as diethyl ether, dipropyl ether, dibutyl ether dipentyl ether, tert-butyl methyl ether (TBME) and the like.

The term "about" comprises the recited number plus or minus up to 10% of that number.

The low temperatures (e.g. −20 to −80° C.) for crystallization of the carotenes can be achieved according to well known methods including emersing a container containing the palm oil/carotenes in a low temperature bath comprising an organic solvent and dry ice or liquid nitrogen. See Gordon, A. J., and Ford, R. A., The Chemist's Companion, a Handbook of Practical Data, Techniques, and References, John Wiley & Sons, New York, N.Y., pp. 451 (1972).

Examples of saponification reagents that can be used in the process include alcoholic solutions comprising a base such as potassium hydroxide, sodium hydroxide and ammonia. The concentration of base in alcohol may range from about 10 wt/vol % to about 30 wt/vol %. Most preferably, the saponification reagent is about 10 wt % methanolic or ethanolic potassium hydroxide.

Nomenclature

The correct systematic name for α-carotene is (6'R)-β,ε-carotene. In this invention, it has been established that the configuration of the stereogenic center at C-6' for α-carotene purified from palm oil is 6'R. However, the absolute configuration of ε,ε-carotene with two stereogenic centers at C-6 and C-6' is not known.

Analysis of Carotenoids By High Performance Liquid Chromatography (HPLC).

The HPLC analysis of carotenoids were conducted according to a published procedure (Khachik et al., *Anal. Chem.* 69:1873–1881 (1997)). The separations were carried out on a Microsorb (25-cm length×4.6 mm i.d.) $C_{18}$ (5-μm spherical particles) column (Rainin Instrument Co., Woburn, Mass.), which was protected with a Brownlee guard cartridge (3-cm length×4.6 mm i.d.) packed with spheri-5-$C_{18}$ (5-μm particle size). A combination of isocratic and gradient HPLC employing a two pump solvent module was used with this eluent. Pump A pumped a mixture of acetonitrile/methanol (9/1, v:v) and pump B pumped a mixture of hexane/dichloromethane/methanol/DIPEA (4.5/4.5/0.99/0.01, v:v:v:v:v). At time zero, an isocratic mixture of acetonitrile (85.5%), methanol (9.995%), dichloromethane (2.25%), hexane (2.25%), and DIPEA (0.005%) (95% pump A, 5% pump B) was pumped for 10 min. After 10 min, a linear gradient was run for 30 min resulting in a final composition of acetonitrile (40.5%), methanol (9.95%), dichloromethane (24.75%), hexane (24.75%), DIPEA (0.055%) (45% pump A, 55% pump B). The column flow rate was 0.70 mL/min. At the end of the gradient, the column was equilibrated under the initial isocratic conditions for 15 min. While carotenoids were quantified at 446 nm, the HPLC runs were also simultaneously monitored at 400, 350, and 290 nm to check for the presence of possible impurities. For a typical HPLC analysis, the purified carotenoids (14 mg) is dissolved in dichloromethane (50 ml) and an aliquot (0.5 ml) of this solution is then diluted to a final volume of 10 ml using the HPLC injection solvents. The HPLC injection solvent consisted of a mixture of acetonitrile (85%), dichloromethane (2.5%), hexane (2.5%), and methanol (10%).

Calculation of the Yield of Carotenoids Purified by Crystallization.

The yield of the isolated carotenoids recovered from crystallization of palm carotene concentrates was based on the concentration of carotenoids in the 2%, 20%, and 30% palm carotene concentrates prior to purification as determined by HPLC analyses of these commercial products. The relative concentration (mg/g) and distribution (%) of carotenoids in crude palm oil and three commercially produced carotene concentrates are shown in Table 1. As indicated earlier, the 2%, 20% and 30% palm carotene concentrate produced by Lion Corporation (Japan) is subjected to extensive purification according to a patented process while the method for the production of the 20% palm carotene concentrate produced in Malaysia is not known.

TABLE 1

The concentration (mg/g) and relative distribution (%) of carotenoids in crude palm oil and three commercially produced carotene concentrates.[a,b]

| Carotenoids | Crude Palm Oil mg/g (%) | 2% Palm Carotene mg/g (%) | 20% Palm Carotene mg/g (%) | 30% Palm Carotene Mg/g (%) |
|---|---|---|---|---|
| (6'R)-β,ε-carotene (all-trans-α-carotene) | 0.14 (19.7) | 3.88 (19.4) | 45.8 (22.9) | 68.4 (22.8) |
| Cis-α-carotene | Not Detected | 1.26 (6.3) | Not Detected | Not Detected |
| All-trans-β-carotene | 0.22 (31.0) | 5.52 (27.6) | 58.4 (29.2) | 102.3 (34.1) |
| 9-cis-β-carotene | 0.15 (21.1) | 4.14 (20.7) | 49.0 (24.5) | 60.9 (20.3) |
| 13-cis-β-carotene | 0.09 (12.7) | 2.76 (13.8) | 11.8 (5.9) | 13.5 (4.5) |
| All-trans-ε,ε-carotene | 0.04 (5.6) | 0.98 (4.9) | 13.8 (6.9) | 13.5 (4.5) |
| All-trans-γ-carotene | 0.07 (9.9) | 1.46 (7.3) | 21.2 (10.6) | 41.4 (13.8) |
| Total | 0.71 (100.0) | 20 (100.0) | 200 (100.0) | 300 (100.0) |

[a]The relative composition of the carotenoids in 20% palm carotene from Lion (Japan) and the product produced in Malaysia is nearly the same.
[b]The values were determined by HPLC on a $C_{18}$-reversed phase column as described in text.

Purification of Carotenes from Palm Oil with 2% Carotene Content

In a typical process, the palm oil with 2% carotene content is first dissolved in an organic solvent such as THF, TBME or similar ethers and is then subjected to alkaline hydrolysis (saponification) e.g. with 10% alcoholic (ethanol or methanol) potassium or sodium hydroxide to remove the oils. The product is partitioned between water and an organic solvent (e.g., hexane, pentane, petroleum ether, tert-butyl methyl ether). The water layer is discarded and the organic layer is washed twice with water containing 10% methanol or ethanol until the pH of the aqueous layer is 7 and all the base is removed. The use of alcohol in the aqueous layer prevents the formation of emulsion. The organic layer is dried, e.g. over sodium sulfate, and evaporated to dryness to give a dark red oil. The oil is treated with an alcohol to remove mostly the cis-carotenes and other alcohol soluble components and the crystalline carotenes are removed by filtration. At this stage the purity of carotenes in the crude product is in the range of 49–55%. This crude solid is then dissolved in the minimum amounts of an organic solvent (e.g., tetrahydrofuran, acetone, a chlorinated solvent) and is treated with an appropriate amount of an alcohol (e.g., methanol, ethanol, 2-propanol) until the solution becomes cloudy. The mixture is kept at about −40° C. or lower for several hours to commence crystallization. The crystalline carotenoids are filtered off, washed with an alcohol, preferably ethanol, and dried under high vacuum to yield a mixture of carotenes in 76–80% purity. The typical composition of carotenes in the alcohol wash, the crude product after saponification, the mother liquor from first crystallization, and the solid product after first crystallization is shown in Table 2.

TABLE 2

The typical composition of carotenoids in various fractions after saponification and first crystallization of carotenes from palm oil with 2% carotene content.[a]

| Carotenoids | Carotenes in Alcohol Wash (%) | Carotenes in Crude Products (%) | Carotenes in Mother Liquor of Crystallization (%) | Carotenes in Product of Crystallization (%) |
|---|---|---|---|---|
| all-trans-α-carotene | 13.6 | 18 | 7.2 | 30 |
| cis-α-carotene[b] | 10.8 | 6 | 12.5 | Not Detected |
| all-trans-β-carotene | 16.5 | 26 | 17.2 | 41 |
| 9-cis-β-carotene | 26.9 | 20.4 | 28.9 | 11 |
| 13-cis-β-carotene | 16.2 | 12.8 | 16.8 | 8 |
| ε,ε-carotene | 7.8 | 6.8 | 9.1 | 2 |
| all-trans-γ-carotene | 8.2 | 10 | 8.3 | 8 |
| Total | 100 | 100 | 100 | 100 |

[a]The values were determined by HPLC on a $C_{18}$-reversed phase column as described in text.
[b]The location of the cis-bond in cis-α-carotene is not known.

As shown in Table 2, the alcohol wash after saponification and the mother liquor from the first crystallization are enriched in substantial amounts of 9-cis-β-carotene, 13-cis-β-carotene, and a cis-isomer of α-carotene. A second crystallization of the solid product from the first crystallization results in a mixture of carotenes in a purity greater than 93%.

Purification of Carotenes from Palm Oil with about 20% to 30% Carotene Content

In the case of the palm oil with about 20% to about 30% carotene content, the above saponification step can be omitted and the oils can be directly subjected to crystallization. In a typical experiment, palm oil is dissolved in tetrahydrofuran (THF), acetone a chlorinated solvent or mixtures thereof. The mixture is stirred for about 15 minutes at room temperature and is treated with an alcohol until the solution becomes cloudy. The solution is kept at about −40° C. or lower for 5 hours and the yellow/orange crystals of palm carotenes are then quickly filtered at −20° C. or lower. The collected crystals are washed with cold alcohol such as methanol or ethanol or 2-propanol or the like. To facilitate the drying process, the crystalline carotenes can be washed with a small amount of cold (−10° C.) acetone. The carotenoid crystals are then dried under high vacuum overnight. Acetone or a combination of acetone and ethanol can also be employed as the crystallization solvents at low temperature (e.g., −10° C.). The identity of the crystallized palm oil carotenoids has been established by comparison of their high performance liquid chromatography (HPLC),and UV-Visible spectra with those of authentic standards.

A variety of other organic solvents and their combinations which have also been successfully employed for the crystallization of palm carotenes at low temperature are listed in Table 3. A second crystallization of the palm carotene in all cases resulted in a mixture of carotenoids which were shown by HPLC to be greater than 95% pure.

The relative distribution of carotenoids in crystallized carotenes and the mother liquor from crystallization of 20% palm oil carotene concentrate which was determined by HPLC is shown in Table 4. According to the HPLC results, considerable amount of 9-cis-β-carotene and 13-cis-β-carotene as well as ε,ε-carotene is removed from crystalline palm carotene and is concentrated in the mother liquor of the first crystallization. However, the ratio of α-carotene to all-trans-β-carotene in the crystalline palm carotene in comparison with the ratio of these compounds in the palm oil carotene concentrate remains nearly unchanged. Therefore the mother liquor from crystallization of concentrated palm oil serves as an excellent source for cis-β-carotene.

TABLE 3

Conditions for purification of carotenoids from two commercially available palm carotene concentrates by crystallization at low temperature.

| The weight (g) of the 20% or 30% Palm Oil Subjected to Crystallization | Crystallization solvent(s), ml | Temp. (° C.) | Weight (g) of the solids and purity (%) of carotenes after the first crystallization[a,b] |
|---|---|---|---|
| 15.1 g of 20% | Acetone, 150 | −10 | 2.00 g, 66% |
| 18.6 g of 20% | Acetone, 200/Ethanol, 100 | −10 | 2.68 g, 72% |
| 23.6 g of 20% | Tetrahydrofuran, 60,/Acetone, 30/Ethanol, 40 | −40 to −60 | 3.68 g, 78% 2.02 g, 72% |
| 14.0 g of 20% | Tetrahydrofuran, 40/Acetone, 25/Methanol, 20 | −60 | 1.89 g, 70% |
| 13.1 g of 20% | Tetrahydrofuran, 34/Acetone, 17/2-Propanol, 22 | | |
| 20.0 g of 20% | Dichloromethane, 80/Ethanol, 30 | −40 to | 2.96 g, 74% |
| 20.0 g of 20% | Dichloromethane, 80/Mthanol, 30 | −60 | 2.80 g, 70% |
| 20.0 g of 20% | Chloroform, 80/Ethanol, 30 | −40 to −60 | 2.84 g, 71% |
| 20.0 g of 20% | 1,2-Dichloroethane, 80/Ethanol, 30 | −40 to −60 | 2.88 g, 72% |
| 10 g of 30% | Acetone, 260 ml | −10 | 2.04 g, 68% |
| 15.5 g of 30% | Acetone, 200 ml/Ethanol, 100 ml | −10 | 4.28 g, 92% |
| 10 g of 30% | Tetrahydrofuran, 125 ml/Ethanol, 200 ml | −40 to −60 | 2.49 g, 83% |
| 13.3 g of 30% | Dichloromethane, 85 ml/Ethanol, 50 ml | −40 to −60 | 3.67 g, 92% |

[a]The purity was determined by HPLC analysis of the purified carotenes.
[b]Upon a second recrystallization under the same conditions, all products were obtained in purity greater than 95%.

TABLE 4

The relative distribution of carotenoids in crystallized carotenes and the mother liquor from crystallization of 20% palm oil carotene concentrate.[a]

| Caretenoids in 20% palm oil carotenes subjected to crystallization | Crystallization solvents | Relative ratio (%) of carotenes in crystallized solids | Relative ratio (%) of carotenes in the mother liquor from crystallization |
|---|---|---|---|
| (6′R)-β, ε-carotene (all-trans-α-carotene) | THF/acetone/EtOH | 32.4 | 16.4 |
| | THF/acetone/MeOH | 34.4 | 11.9 |
| | THF/acetone/2-propanol | 33.8 | 17.0 |
| | CH$_2$Cl$_2$/EtOH | 32.0 | 15.0 |
| | Acetone/EtOH | 32.0 | 14.0 |
| cis-α-carotene[b] | THF/acetone/EtOH | N.D.[c] | 10.0 |
| | THF/acetone/MeOH | N.D.[c] | 12.8 |
| | THF/acetone/2-propanol | N.D.[c] | 9.4 |
| | CH$_2$Cl$_2$/EtOH | N.D.[c] | 11.0 |
| | Acetone/EtOH | N.D.[c] | 10.0 |
| all-trans-β-carotene | THF/acetone/EtOH | 47.1 | 18.3 |
| | THF/acetone/MeOH | 42.7 | 14.6 |
| | THF/acetone/2-propanol | 46.3 | 19.1 |
| | CH$_2$Cl$_2$/EtOH | 46.5 | 17.0 |
| | Acetone/EtOH | 47.0 | 16.0 |
| 9-cis-β-carotene | THF/acetone/EtOH | 5.6 | 34.1 |
| | THF/acetone/MeOH | 6.9 | 32.8 |
| | THF/acetone/2-propanol | 4.7 | 33.7 |
| | CH$_2$Cl$_2$/EtOH | 5.1 | 35.0 |
| | Acetone/EtOH | 5.2 | 36.0 |
| 13-cis-β-carotene | THF/acetone/EtOH | 2.6 | 8.9 |
| | THF/acetone/MeOH | 2.9 | 14.0 |
| | THF/acetone/2-propanol | 2.3 | 8.5 |
| | CH$_2$Cl$_2$/EtOH | 2.5 | 9.2 |
| | Acetone/EtOH | 2.2 | 11.0 |
| ε,ε-carotene | THF/acetone/EtOH | 1.1 | 8.7 |
| | THF/acetone/MeOH | 1.5 | 10.1 |
| | THF/acetone/2-propanol | 0.8 | 8.6 |
| | CH$_2$Cl$_2$/EtOH | 1.4 | 9.1 |
| | Acetone/EtOH | 1.2 | 10.0 |
| γ-carotene | THF/acetone/EtOH | 11.2 | 3.6 |
| | THF/acetone/MeOH | 11.6 | 3.8 |
| | THF/acetone/2-propanol | 12.1 | 3.7 |
| | CH$_2$Cl$_2$/EtOH | 12.5 | 3.7 |
| | Acetone/EtOH | 12.4 | 3.0 |

[a]The ratio of carotenoids was determined by HPLC.
[b]Tentatively identified; the location of the cis-bond is not known.
[c]Not detected.

The following examples are illustrative, but not limiting, of the processes of the present invention. Other suitable modifications and adaptations of the variety of conditions and reagents normally encountered in natural products chemistry and which are obvious to those skilled in the art are within the spirit and scope of the invention.

EXAMPLES

Example 1

Saponification and Crystallization of Carotenoids From Palm Oil With 2% Carotene Content 10 g of Palm carotene with 2% total carotenoid content (The Lion Corporation of Japan) was dissolved in tetrahydrofuran (40 ml) and was treated with 40 ml of methanolic KOH (10%). The mixture was stirred at room temperature for 7 hours; during this time an oil was gradually formed which slowed down the stirring of the solution. The stirring speed was increased in order to ensure complete mixing of the reaction mixture. After 7 h, the product was treated with hexane (50 ml) and water (50 ml) and the mixture was transferred into a separatory funnel and, after vigorously mixing, the aqueous and organic phases were allowed to separate for a few minutes. The aqueous layer was dark yellow and the organic layer was dark red. A pale yellow oil-like material was also formed between the two layers which was removed and discarded with the aqueous layer. The organic phase was washed with 50 ml of water containing 10% methanol. The addition of methanol prevented the formation of emulsion. The aqueous layer and the oil-like materials between the aqueous phase and the organic phase were removed and washing with methanol/water (10%) was repeated one more time until the pH of the aqueous phase was 7. The organic phase was dried over sodium sulfate, and evaporated to dryness to give 1.0 g of a dark red oil. The oil was washed twice with ethanol (2×15 ml) and the mixture was centrifuged at 3000 rpm for 5 minutes. The combined supernatant liquid was removed from the red solid. The weight of the ethanol soluble material was approximately 0.6 g. According to HPLC the supernatant liquid consisted of a total of 16.3 mg of carotenes comprising of a mixture of γ-carotene (8.2%), ε,ε-carotene (7.8%), α-carotene (13.6%), cis-α-carotene (10.8%), all-trans-β-carotene (16.5%), 9-cis-β-carotene (26.9%), and 13-cis-β-carotene (16.2%).

The red solid (0.4 g, 49% purity) was shown by HPLC to consist of a mixture of γ-carotene (10%), ε,ε-carotene (6.8%), α-carotene (18%), cis-α-carotene (6%), all-trans-β-carotene (26%), 9-cis-β-carotene (20.4%), and 13-cis-β-carotene (12.8%). Crystallization from acetone (1 ml) and ethanol (10 ml) at −15° C. followed by removal of the solvents and drying under high vacuum overnight gave 0.20 g of a mixture of γ-carotene (8%), ε,ε-carotene (2%), α-carotene (30%), all-trans-β-carotene (41%), 9-cis-β-carotene (11%), and 13-cis-β-carotene (8%) in 80% purity. At this stage, the recovery of carotenoids based on the starting material (palm oil with 2% carotene content) was 80%. A subsequent crystallization of the solids with acetone and alcohol gave a mixture of carotenes in 95% purity.

The mother liquor from first crystallization was shown to consist of γ-carotene (8.3%), ε,ε-carotene (9.1%), α-carotene (7.2%), cis-α-carotene (12.5%), all-trans-β-carotene (17.2%), 9-cis-β-carotene (28.9%), and 13-cis-β-carotene (16.8%).

Example 2

27.3 g of Palm carotene with 2% total carotenoid content was dissolved in tetrahydrofuran (300 ml) and was treated with 100 ml of ethanolic KOH (10%) for 16 h. The product was partitioned between hexane (200 ml) and water (200 ml) and the mixture was vigorously shaken. The aqueous layer was removed and discarded; the organic phase was washed twice with 100 ml of water containing 10% ethanol. The organic phase was dried over sodium sulfate, and evaporated to dryness to give 1.9 g of a dark red oil. The oil was washed twice with ethanol (2×25 ml) and centrifuged at 3000 rpm for 5 minutes. The combined supernatant liquid was removed from the red solid. The weight of the ethanol soluble material was 1.0 g. The red solid (0.9 g, 55% purity) was shown by HPLC to consist of γ-carotene (9%), ε,ε-carotene (4%), α-carotene (27.6%), all-trans-β-carotene (29.7%), 9-cis-β-carotene (18%), and 13-cis-β-carotene (11.7%). The solid was dissolved in 8 ml of THF and then treated with 16 ml of ethanol. The mixture was kept at −40° C. for six hours to crystallize the carotenes and was then centrifuged at 3000 rpm for 5 minutes. The solvent was removed and the red crystals were washed with cold ethanol (10 ml) and dried under high vacuum overnight to give (0.55 g) of a mixture of γ-carotene (8.1%), ε,ε-carotene (2.5%), α-carotene (31.4%), all-trans-β-carotene (40.3%), 9-cis-β-carotene (10%), and 13-cis-β-carotene (7.7%) in 76% purity. The recovery of carotenes based on the starting material (palm oil with 2% carotene content) was approximately 77%. A subsequent crystallization from THF and alcohol gave a mixture of carotenes in 93% purity.

The mother liquor from this crystallization was shown by HPLC to consist of a mixture of γ-carotene (7.5%), ε,ε-carotene (6.5%), α-carotene (14.6%), cis-α-carotene (9.1%), all-trans-β-carotene (20.4%), 9-cis-β-carotene (25.6%), and 13-cis-β-carotene (16.3%) in approximately 55% purity.

Example 3

Crystallization of Carotenoids From Palm Oil With 20% Carotene Content

A well-homogenized sample of concentrated palm oil with 20% carotene content (23.6 g) (The Lion Corporation of Japan) was completely dissolved in 60 ml of tetrahydrofuran (THF) and acetone (30 ml) by vigorous stirring at room temperature for 15 minutes. Ethanol (40 ml) was added and the mixture was stirred at room temperature for a few minutes followed by cooling in a Dry-Ice/acetone bath at −40° C. to −60° C. for 5 h. The yellow/orange crystals were filtered at −20° C. or lower. The crystals were successively washed with cold (−10° C.) ethanol (20 ml) and cold (−10° C.) acetone (20 ml) and dried under high vacuum at 0.01 mm/Hg at room temperature overnight. This gave 3.68 g (78%) of dark orange crystals of palm carotenes.

Example 4

A well-homogenized sample of concentrated palm oil with 20% carotene content (20 g) was completely dissolved in 80 ml of dichloromethane by vigorous stirring at room temperature for 15 minutes. Ethanol (30 ml) was added and the mixture was stirred at room temperature for a few minutes followed by cooling in a Dry-Ice/acetone bath at −40° C. to −60° C. for 5 h. The yellow/orange crystals were filtered at −20° C. or lower. The crystals were successively washed with cold (−10° C.) ethanol (20 ml) and cold (−10° C.) acetone (20 ml) and dried under high vacuum at 0.01 mm/Hg at room temperature overnight. This gave 2.96 g (74%) of dark orange crystals of palm carotenes.

Example 5

Crystallization of Carotenoids From Palm Oil With 30% Carotene Content

Concentrated palm oil with 30% carotene content (The Lion Corporation of Japan) was homogenized by stirring and 10 g of this suspension was weighed out and treated with 260 ml of acetone. The mixture was vigorously stirred at ambient temperature for 30 minutes. The carotenoids immediately appeared as a suspension while the oil dissolved in acetone. The mixture was then cooled at −10° C. for 5 hours and filtered. The crystals of carotenoids was washed with 50 ml of cold acetone (−10° C.) and dried under high vacuum at 0.01 mm/hg and room temperature overnight to give 2.04 g (68%) of dark orange crystals.

Example 6

Concentrated palm oil with 30% carotene content was homogenized by stirring and 10 g of this suspension was weighed out and treated with 125 ml of tetrahydrofuran. The mixture was vigorously stirred at ambient temperature for 15 minutes. Ethanol (200 ml) was added and the mixture was stirred at room temperature for a few minutes followed by cooling in a Dry-Ice/acetone bath at −40° C. to −60° C. for 5 h. The yellow/orange crystals were filtered at −20° C. or lower. The crystals were successively washed with cold (−10° C.) ethanol (20 ml) and cold (−10° C.) acetone (20 ml) and dried under high vacuum at 0.01 mm/Hg at room temperature overnight. This gave 2.49 g (83%) of dark orange crystals of palm carotene. Example 7

Crystallization of Carotenoids From Palm Oil With 13.1% Carotene Content 10.4 g of Palm carotene with 13.1% total carotenoid content (The Lion Corporation of Japan) was dissolved in THF (50 ml) and acetone (30 ml) with vigorous stirring. Ethanol (220 ml) was added and the mixture was kept at 0° C. for 4 h. The orange solid was collected by filtration to give 3.23 g of impure carotenes. This was re-dissolved in THF (12 ml) and ethanol (75 ml) was added. The mixture was kept at 0° C. for several hours and was filtered to give 2 g (wet weight) dark orange crystals of carotenes. This was dried under high vacuum to a constant weight of 1.1 g.

Having now fully described this invention, it will be understood by those of ordinary skill in the art that the same can be performed within a wide and equivalent range of palm oils, conditions, other parameters without affecting the scope of the invention or any embodiment thereof. All patents, patent applications and publications cited herein are fully incorporated by reference herein in their entirety.

What is claimed is:

1. A process for isolation of a mixture of carotenes from palm oil, comprising, dissolving the palm oil in an organic solvent, saponifying the organic solution of the said palm oil with an alcoholic solution of a mineral base; washing the organic layer with water containing about 10–20% alcohol until the base is removed, separating and concentrating the resultant organic phase comprising isolated carotenes; and washing the separated carotenes with an alcohol thereby obtaining crystallized carotenes.

2. The process of claim 1, wherein said palm oil contains about 2 to about 30 wt % carotenes.

3. The process of claim 1, wherein said crystallized carotenes comprise α-carotene (about 30%), all-trans-β-carotene (about 41%), 9-cis-β-carotene (about 11%), 13-cis-β-carotene (about 8%), ε,ε-carotene (about 2%), and γ-carotene (about 8%).

4. The process of claim 1, wherein said palm oil comprises about 2 wt % carotenes is dissolved in an organic solvent, said aqueous base is about 10% potassium or sodium hydroxide in methanol or ethanol, and the separated carotenes are washed with an alcohol to obtain crystallized carotenes having a purity of about 49–55%.

5. The process of claim 4, wherein said organic solvent is tetrahydrofuran (THF) or tert-butyl methyl ether (TBME).

6. The process of claim 1, further comprising recovering the alcohol wash to give a solution comprising a mixture of 9-cis-β-carotene, 13-cis-β-carotene, a cis-isomer of α-carotene, ε,ε-carotene, and γ-carotene.

7. The process of claim 4, wherein said crystallized carotenes having a purity of about 49–55% are recrystallized from a mixture of acetone and an alcohol at −15° C. or lower to obtain a crystalline mixture of carotenes having about 76–80% purity, and further subjecting the crystalline mixture of carotenes to a second recrystallization with a mixture of acetone and an alcohol to increase the purity of carotenes to 93% or greater.

8. The process of claim 4, wherein said crystallized carotenes having a purity of about 49–55% are recrystallized from a mixture of tetrahydrofuran (THF) and an alcohol at −40° C. or lower to obtain a crystalline mixture of carotenes having about 76–80% purity, and further subjecting the crystalline mixture of carotenes to a second recrystallization with a mixture of THF and an alcohol to increase the purity of carotenes to 93% or greater.

9. The process of claim 4, wherein said crystallized carotenes having a purity of about 49–55% are recrystallized from a mixture of a chlorinated solvent and an alcohol at −40° C. or lower to obtain a crystalline mixture of carotenes having about 76–80% purity, and further subjecting the crystalline mixture of carotenes to a second recrystallization with a mixture of acetone and an alcohol to increase the purity of carotenes to 93% or greater.

10. The process of claim 9, wherein said chlorinated solvent is chloroform, dichloromethane or 1,2-dichloroethane.

11. The process of any one of claims 7–9, wherein said alcohol is methanol, ethanol or 2-propanol.

12. The process of any one of claims 7–9, further comprising recovering the alcohol wash from the recrystallization(s) to give a solution comprising a mixture of 9-cis-β-carotene, 13-cis-β-carotene, a cis-isomer of α-carotene, ε,ε-carotene, and γ-carotene.

13. The method of claim 1, further comprising micronizing said crystalline carotenes into water dispersable beadlets.

* * * * *